(12) United States Patent
Sisti

(10) Patent No.: US 8,616,073 B2
(45) Date of Patent: Dec. 31, 2013

(54) SAMPLER FOR ELEMENTAL ANALYZERS

(75) Inventor: Leonardo Sisti, Pavia (IT)

(73) Assignee: Eurovector S.p.A., Milan (IT)

( * ) Notice: Subject to any disclaimer, the term of this patent is extended or adjusted under 35 U.S.C. 154(b) by 665 days.

(21) Appl. No.: 12/849,660

(22) Filed: Aug. 3, 2010

(65) Prior Publication Data
US 2011/0030485 A1   Feb. 10, 2011

(30) Foreign Application Priority Data
Aug. 7, 2009   (IT) .............................. MI2009A1440

(51) Int. Cl.
*G01N 1/22* (2006.01)

(52) U.S. Cl.
USPC ...................................... 73/863.11

(58) Field of Classification Search
USPC ............................. 73/19.01–19.12
See application file for complete search history.

(56) References Cited

U.S. PATENT DOCUMENTS

| | | | |
|---|---|---|---|
| 4,336,721 A | | 6/1982 | Curtis |
| 5,447,077 A | * | 9/1995 | Lautenschlager .......... 73/863.11 |
| 5,866,072 A | | 2/1999 | Bowe, Jr. et al. |
| 5,981,290 A | * | 11/1999 | Lyon et al. .................... 436/157 |

FOREIGN PATENT DOCUMENTS

WO    WO 03/025560 A2    3/2003

OTHER PUBLICATIONS

P.J. Polissar et al., "Measurement of 13C and 15N Isotopic Composition on Nanomolar Quantities of C and N." Analytical Chemistry, vol. 81(2), pp. 755-763, Jan. 15, 2009. (Abstract).
M.S. Filot, et al., "Rabid Online Equilibration Method to Determine the D/H Ratios of Non-Exchangeable Hydrogen in Cellose." Rapid Communications in Mass Spectrometry, vol. 20 (22), pp. 3337-3344, 2006. (Abstract).
P.E. Sauer, et al, "Simplified Batch Equilibration for D/H Determination of Non-Exchangeable Hydrogen in Solid Organic Material." Rapid Communications in Mass Spectrometry, vol. 23, pp. 949-956, 2009.

* cited by examiner

*Primary Examiner* — Peter Macchiarolo
*Assistant Examiner* — Alex Devito
(74) *Attorney, Agent, or Firm* — Dickstein Shapiro LLP

(57) ABSTRACT

A sampler for an elemental analyzer comprises a sample housing suitable to accommodate one or more samples, sealed in tin or silver capsules, to be analyzed, a closure mechanism suitable to reversibly seal the sample housing, a sample passage having a connection opening for the passage by gravity of the one or more samples from the sampler into the analyzer through the connection opening. The sampler further comprises a heater for heating the sample housing and a vacuum system or other means for pumping out environmental gases and vapors from the sample housing.

20 Claims, 5 Drawing Sheets

SAMPLER FOR ELEMENTAL ANALYZERS

BACKGROUND OF THE INVENTION

1. Field of the Invention

The present invention relates to a sampler for automatic elemental analyzers including a pyrolytic unit, particularly a sampler of the fully tight, sealed type.

2. Description of the Related Art

An elemental analyzer, including a pyrolytic unit internally or aside, is an instrument intended for analyzing the elemental composition in samples of solid or liquid materials, usually accommodated in e.g. tin or silver cups using oxygen for combustion and carbon for pyrolytic reduction generating gas as reaction products. An elemental analyzer comprises a sampler for introducing the sample suitably prepared e.g. in said tin or silver cups or adsorbed in inert material if liquids into a combustion or pyrolytic reactor of the analyzer itself. The elemental analyzer further comprises a furnace in which reactor tubes for combustion (usually at temperatures higher than 900° C.) or pyrolytic reaction (usually at temperatures between 1200-1500° C. or more) are accommodated for sample combustion or pyrolysis.

Samples thus converted into a gas mixture flow through a trap to eventually eliminate water or acidic gas and a gas chromatography column which allows the gas to be time separated and then detected by a TCD for stand alone application providing element % result in the mixture; the separated gas can be further analyzed in their isotopic composition entering in continuous flow in an Isotopic Ratio Mass Spectrometer to provide Isotopic Ratio composition of the isotopes included in each element. A pneumatic circuit is provided capable of creating a continuous flow of carrier gas, for example Helium or Argon.

Many sampler are known in the art.

An example of a known non-sealed type of sampler is disclosed in the Utility model no. TO2001 U 000175 in the name of the present Applicant.

A problem of the known samplers for elemental analyzers used in combustion or pyrolysis is that samples can contains traces of residual adsorbed gas, water, vapor or other compound present on the samples as they are, or resulting from pre-treatments or storage. These unwanted material can affect element % results in stand alone combustion and pyrolytic application and indeed isotopic ratio accuracy.

SUMMARY OF THE INVENTION

The object of the present invention is therefore to provide a sampler suitable to eliminate air contamination affecting Nitrogen and Oxygen determination, all other environmental components and gas, vapor, volatile components adsorbed or present in the samples affecting results and to mitigate or at least partially overcome the drawbacks mentioned with reference to the samplers according to the known prior art.

Particularly, it is an object of the present invention to provide a sampler suitable to at least partially eliminate in the standardize conditions the gas species adsorbed in the sample or cup container or in the environment or traces of any residual volatile substance present in the sampler before the samples are introduced into the analyzer together with cups or other means.

Another object of the present invention is to allows simultaneous preparation of the samples inside the sampler in the same conditions.

These and other objects are achieved by a sampler according to claim 1. Each of the dependant claims defines a possible embodiment of the sampler according to the invention.

A further object of the present invention is to allow simultaneous injection of equilibration liquid in the sampler housing for simultaneous equilibration of all samples included in the sampler.

This and other objects are achieved by a sampler according to claim 17.

BRIEF DESCRIPTION OF THE DRAWINGS

In order to better understand the invention and appreciate the advantages thereof, some exemplary, non-limiting embodiments thereof are described below, with reference to the annexed Figures, in which.

DETAILED DESCRIPTION OF THE PREFERRED EMBODIMENTS

Figure 2:
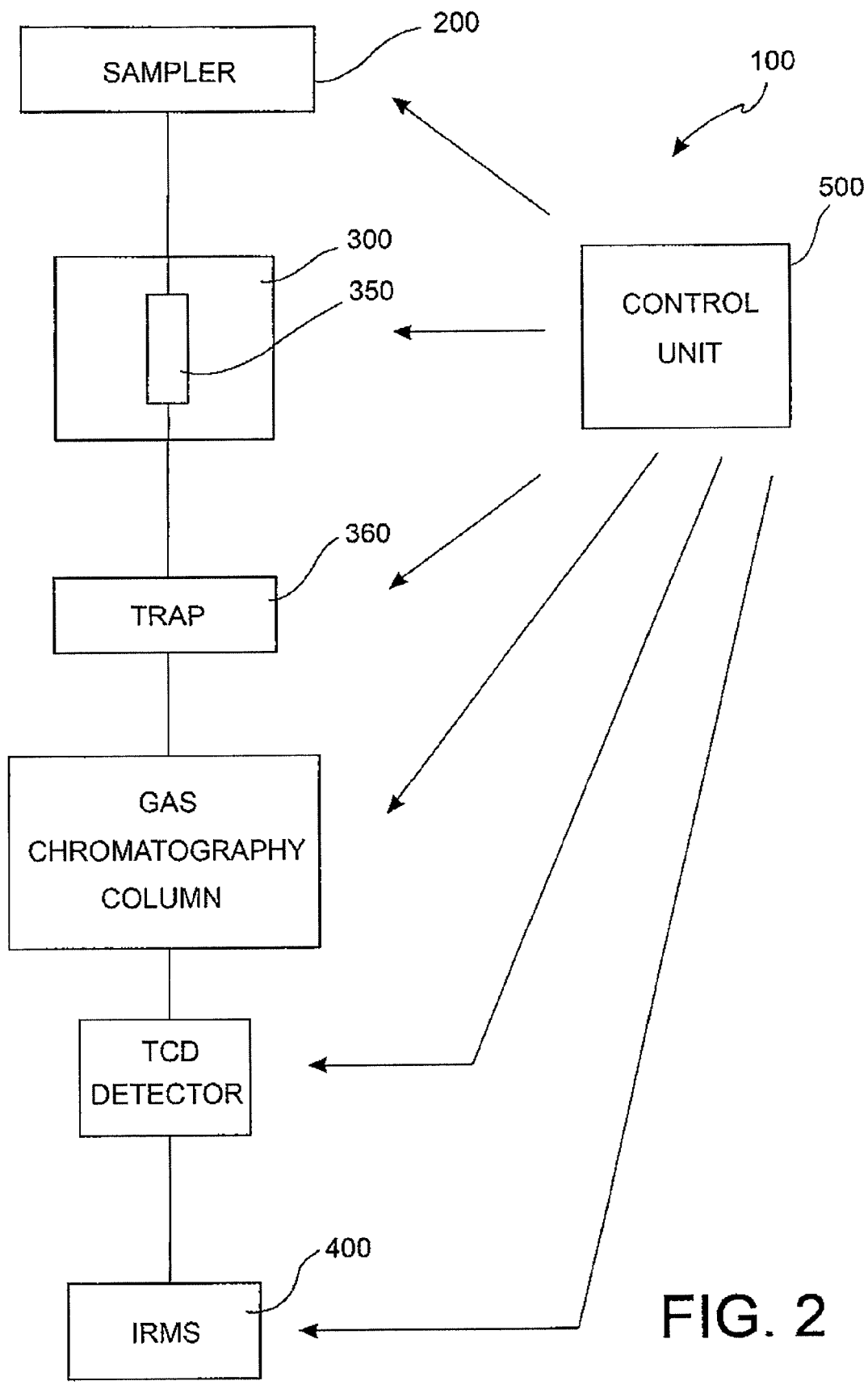
FIG. 2 is a functional schematic view of an elemental analyzer comprising a sampler according to the invention.

With reference to the annexed FIG. 2, an elemental analyzer is indicated with the reference number 100. An elemental analyzer is an instrument intended for analyzing the elemental composition of liquid or solid samples providing results as % of each element using a TCD Detector in stand alone or results as isotopic ratio using in series an isotopic ratio mass spectrometer IRMS.

The elemental analyzer 100 comprises a sampler 200 whose task is to introduce the sample to be analyzed and generally filled in tin or silver cups into a system comprising a furnace 300 in which it is usually accommodated a reaction tube 350 and brought to a temperature of about 900° C. or more for combustion applications and between 1200° C.-1500° C. or more for pyrolytic applications, which is thus combusted in presence of Oxygen or converted by Carbon Reduction, providing a gas mixture suitable to be detected by the TCD in stand alone and/or the isotopic ratio mass spectrometer IRMS when this detector is interfaced. Gas species produced in the Combustion or Pyrolytic Reduction are coming out from the reaction tube and are flowing into a trap 360 to eliminate undesired acidic gases or water and are than time separated by gas chromatography to obtain peaks of single elements directly related to % composition or isotopic ratio determination.

A control unit 500 drives the various components of the analyzer 100.

The focus of the present invention is on the sampler 200.

Figure 1:
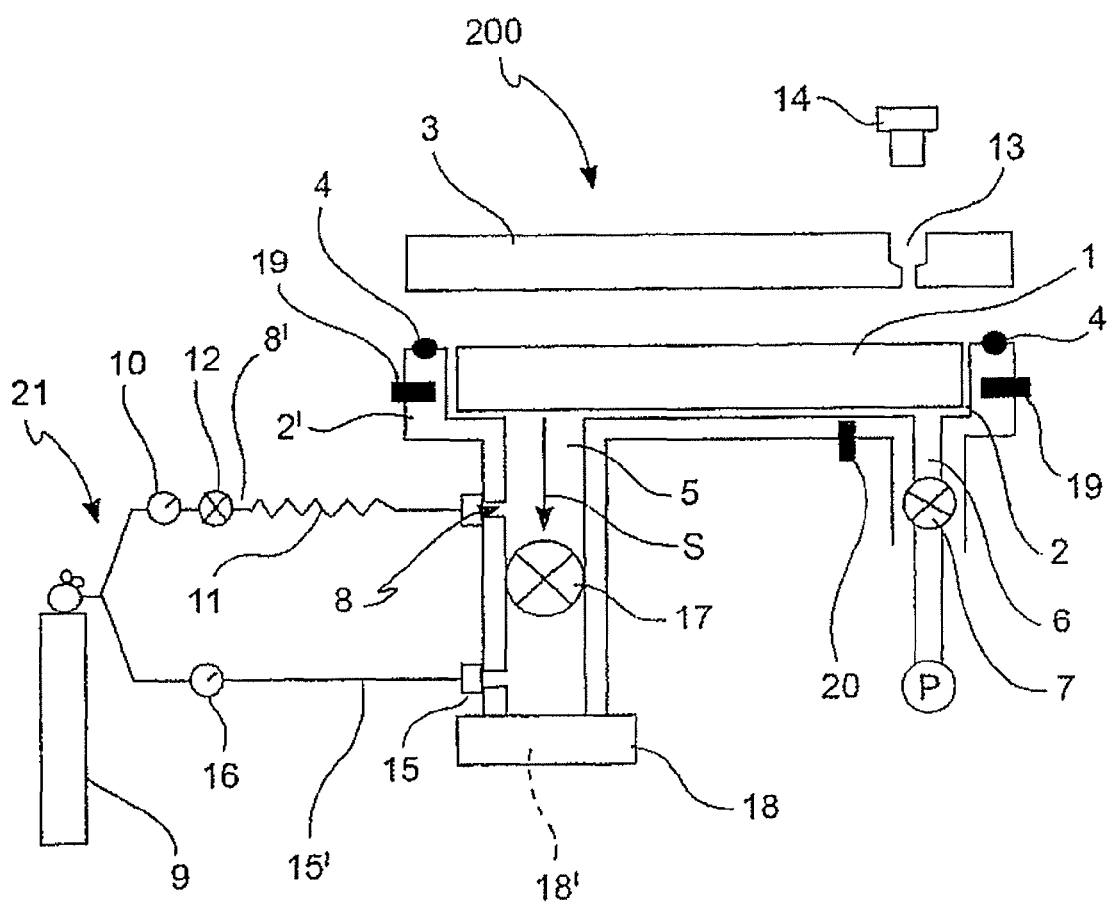
FIG. 1 is schematic side view of a sampler according to a first embodiment of the invention.

With reference to the annexed FIG. 1, the sampler 200 according to the invention comprises a sample housing 2 suitable to accommodate one or more samples as sequence (not shown in the figures). The sample housing 2 is preferably delimited by a sample housing body 2' of the sampler 200. In accordance with an embodiment, a sample carousel 1 is provided, on which the samples, generally sealed in tin or silver caps, are loaded.

The sampler 200 comprises closure means suitable to reversibly seal the sample housing 2, so that, after the samples are accommodated, the closure means can be closed and the samples in the carousel 1 cannot be further contaminated by environmental agents due to the specific design granting full tightness. For example, the closure means may comprise a plate 3 acting as a lid for the sample housing 2. Tightening means are provided in order to form a gastight enclosure when the lid 3 closes the sample housing 2. In accordance with a possible embodiment, the tightening means comprise an O-ring 4 providing a gas tightness between the sample housing 2 and the external environment when the plate 3 rests on the sample housing body 2', thereby closing the sample housing 2. The whole design ensures an absolute "Zero Blank" for the environmental contamination as proved by sampling from the carousel without samples by using IRMS as supersensitive measure to the contamination by using the corresponding mass of the contaminating agent (e.g. mass of $N_2$).

The sampler 200 further comprises a sample passage 5 for the passage of the samples loaded in the sample housing 2 into the analyzer. The sampler is connected or connectable to the analyzer 100 by means of a connector 18 provided with a connection opening 18'. The sample passage 5 is preferably located in the lower part of the sample housing 2, so to allow the samples to drop by gravity from the sample housing 2 to the analyzer through the connection opening 18' (see arrow S in FIG. 2).

Advantageously, the carousel 1 is able to advance by discrete steps, for example pneumatic or electrical actuated, so to drop each individual sample to be analyzed sequentially from the carousel 1 and to bring it directly above the sample passage 5 at an appropriate time during the analysis cycle.

Advantageously, the sampler 200 comprises means, such as vacuum system, for pumping environmental gases and vapours out of the sample housing 2 and/or means for heating the sample housing 2 itself and the one or more samples loaded therein. These pumping means may alternatively be included within the sampler or be externally located and connectable to the latter.

The heating means preferably comprise a plurality of heaters 19, still more preferably inserted into the sample housing body 2', in such a manner that they are able to heat the sampler body, the carousel and in turn the sample cups and samples itself by heat conduction. The heating means may further comprise a temperature sensor 20, which may be in turn inserted in the sample housing body 2' and may be connected to the control unit 500. In this manner, the control unit 500 is capable of receiving a temperature signal from the temperature sensor 20 thereby controlling the heaters 19 so to maintain the temperature inside the sample housing 18 at a constant desired value.

Figure 3:
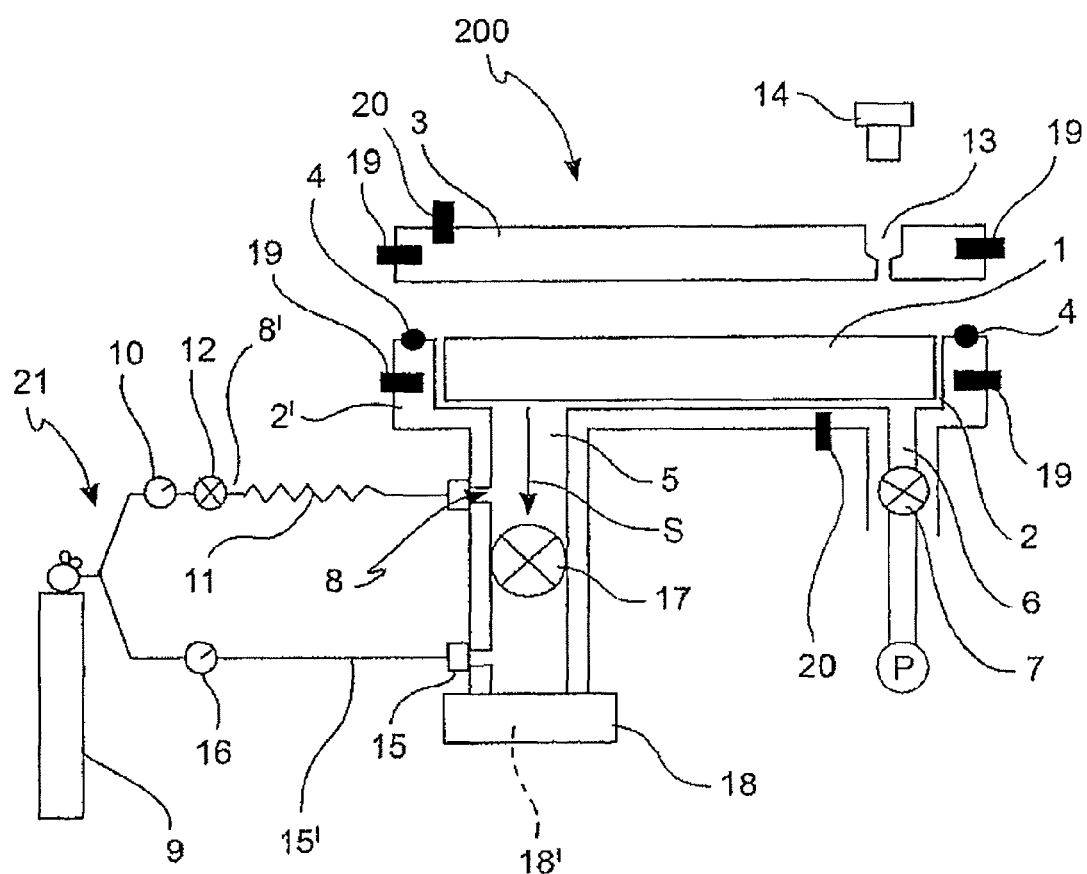
FIG. 3 is a schematic side view of a sampler according to a second embodiment of the invention.

According to a second embodiment of the invention shown in annexed FIG. 3, heaters 19 and temperature sensors 20 are also inserted into closure plate 3. In this way it is possible to avoid vapour condensation. The pumping means may comprise a pump P and are advantageously suitable to generate a vacuum inside the sample housing 2'. In this manner the atmospheric gases, water and tension volatile compound at the increased vapour temperature due to heat application will allow the process to work far more effectively. Depending on the selection of the parameter related to heat and vacuum application optimal conditions for the different variety of sample can be selected with gas pumped away from the sample housing 2, such that the isotopic composition accuracy can be improved and troublesome inconveniences limited.

In accordance with a possible embodiment, the sampler 200 comprises a pumping duct 6, preferably located in the lower part of the sample housing 2 to allow the fluid connection of the latter with the pump P.

Advantageously, in the pumping duct 6 pump isolation valve means are provided. In particular, such pump isolation valve means include a pump isolation valve 7 operatively located between the pump P and the sample housing 2. As further advantage, the pump isolation valve 7 is configurable in at least an open configuration and in a close configuration. When the pump isolation valve 7 is in the open configuration, the pump P and the sample housing 2 are in fluid connection, so that gases in the sample housing can be evacuated by the pump P. Instead, when the pump isolation valve 7 is in the closed position, the sample housing 2 and the pump P are not in fluid communication, such that the sample housing is isolated from the pump P. Preferably, the pump isolation valve 7 is of the ON/OFF type.

Advantageously, the sampler 200 comprises a inert gas circuit 21. Alternatively, the sampler 200 is connected or connectable to said inert gas circuit 21.

According to an embodiment, the inert gas circuit 21 comprises a flushing duct 8' which is connected or connectable to the sample passage 5 at a first gas port 8. The flushing duct 8' is further connected or connectable to a gas cylinder 9 suitable to accommodate pressurized inert gas, for example Helium or Argon. In this manner the inert gas is able to flow from the gas cylinder 9 to the sample housing 2 through the flushing duct 8'.

Advantageously, the closure plate 3 comprises a gas vent 13 having a purge plug 14 which allows the reversible closure of the gas vent 13. In this manner, when the gas vent 13 is open, the sample housing 2 can be purged from the atmospheric gases and the samples in the sample housing 2 can be maintained in an inert gas environment with a fully sealed enclosure. It has to be noted that the heating means help the purge process of the Helium. In fact, Helium flows into the cups which are closed but not sealed. Adsorbed gas in geological material or hygroscopic cellulose as important examples as well other pre-treated samples, will release gas or water more efficiently helped by purge action of the most diffusive Helium and temperature application also helping dry sample to remain dry during an autorun full sequence.

Advantageously, the flushing duct 8' comprises gas cylinder isolation valve means which are operatively interposed between the gas cylinder 9 and the sample housing 2, particularly, between the gas cylinder 9 and the sample passage 5. The gas cylinder isolation valve means preferably comprise a gas cylinder isolation valve 12 which is configurable in at least an open configuration, in which the gas cylinder 9 is in communication with the sample housing 2, particularly with the sample passage 5 which is connected with the sample housing 2, and a close position, in which the gas cylinder 9 is isolated from the sample passage. Still more preferably, the gas cylinder isolation valve 12 is an ON/OFF type valve, such that the admission of the inert gas coming from the gas cylinder 9 into the sample passage 5 and the sample housing 2 can be switched on and off.

In accordance with a possible embodiment, the flushing duct 8' comprises gas restriction means 11 and a pressure regulator 12. The pressure regulator 10 has the function of controlling the rate of admission of the inert gas into the sample housing 2, whilst the gas restriction means have the function of slowing the gas flow into the sample housing 2.

In accordance with an embodiment, the inert gas circuit 21 comprise a carrier gas duct 15' connected or connectable to the gas cylinder 9 and connected or connectable to the sample passage 5, particularly at a second gas port 15, in such a manner that the pressurized gas form the gas cylinder 9 is capable of passing through the sample passage 5, particularly towards the connection opening 18'.

Advantageously, the carrier gas duct 15' is operatively in parallel with the flushing duct 8'. Still more advantageously, the carrier gas duct 18' comprises a pressure regulator 16, such that the rate of admission of the inert gas into the sample passage 5 can be controlled.

With further advantage, the sample passage 5 comprises sampler isolation valve means, particularly a sampler isolation valve 17, located in the sample passage 5 itself between the first 8 and the second 15 gas ports, the latter gas port 15 being interposed between the sampler isolation valve 17 and the connection opening 18'. The sampler isolation valve 17 is configurable in at least an open configuration and in a close configuration. To this purpose, the sampler isolation valve is preferably a valve of the ON/OFF type. In this manner, the sampler isolation valve 17 allows the sampler 200 to be isolated from elemental analyzer, particularly a carrier gas circuit thereof (not shown in the figures), when the sampler is connected to the elemental analyzer.

Figure 4:
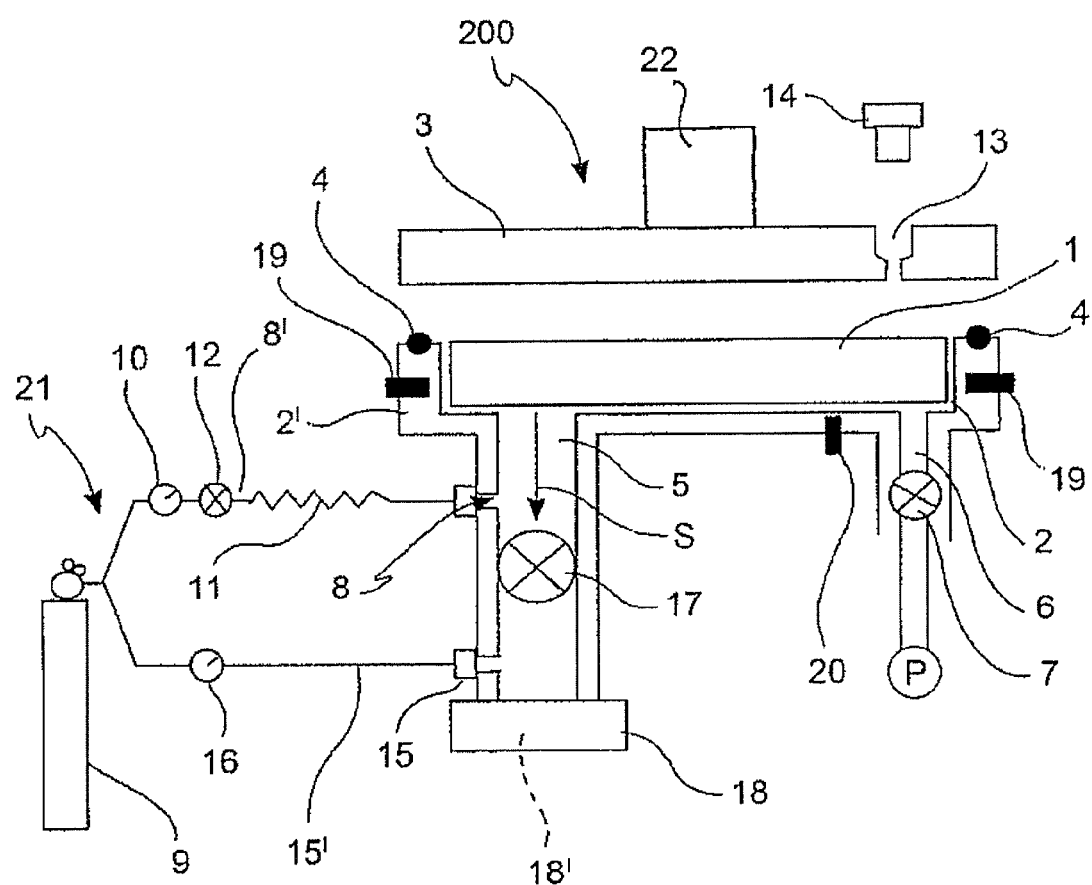
FIG. 4 is a schematic side view of a sampler according to a third embodiment of the invention.

According to a third embodiment of the invention shown in FIG. 4, sampler 200 is provided with an injection unit 22 which allows injection of liquids in the sample housing 2 inside the sampler 200. As a matter of fact, several analysis of organic material requires the use of a liquid. In such cases, the known prior art requires a pre-treatment of the samples which are added with such liquids before being inserted into the sampler and usually are pre-treated one after the other. On the contrary, the injection unit 22 allows the liquid to be injected directly in the sample housing 2 of sampler 200 by a single injection for all the samples in the same condition without the need of removing the samples, thus the samples are treated substantially simultaneously and the results of the analysis are reliable.

Example of analysis which requires the injection of liquids are: studies of paleoclimate, animal migration, forensic, food and flavor authentication, origin and diagenesis of organic material, complex organic materials such as feathers or keratin. In these cases it is necessary to equilibrate the samples with water at known isotopic composition.

According to the third embodiment of the invention such equilibration treatment is carried out inside sampler 200.

Preferably, the injection unit 22 comprises an injection port, in fluid communication with the sample housing 2 and thus with the samples; a septum through which the liquid is injected in the injection port preferably by using a syringe; a septum holder.

Preferably the liquid comprises water at known Isotope Ratio.

Both the syringe and the septum may be chosen on the basis of the test to be performed. They may be of any suitable known type and thus they will be no further described.

Figure 5:
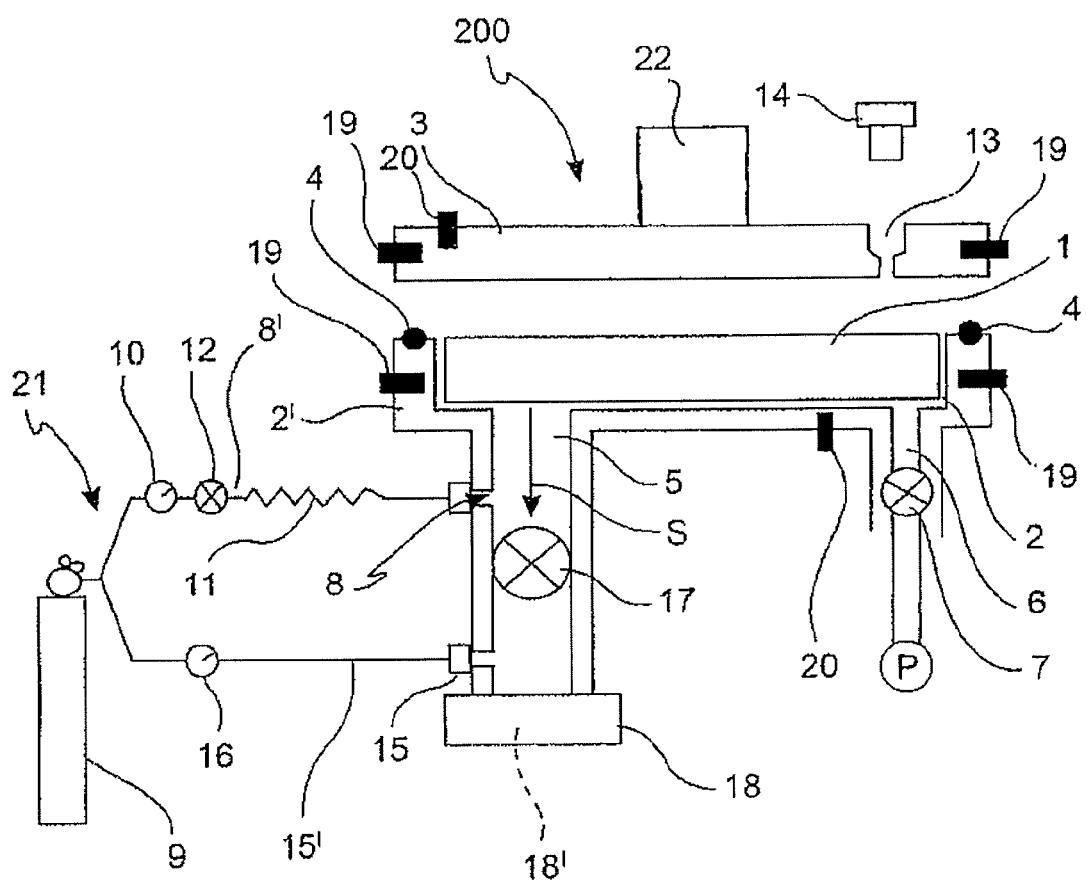
FIG. 5 is a schematic side view of a sampler according to a forth embodiment of the invention.

According to a forth embodiment of the invention shown in FIG. 5, heaters 19 and temperature sensors 20 are provided both in the sample housing body 2' and into closure plate 3. Furthermore sampler 200 is provided with an injection unit 22.

With reference to the annexed figures, possible operating modes of the sampler according to the invention will be described.

A first possible operating mode is a "degassing mode", in which the environmental gas contaminants (e.g Oxygen from air with different composition from Oxygen in the sample or water in hygroscopic material at different isotopic composition from Oxygen included for instance in Cellulose) are purged away; samples to be analyzed, filled into tin or silver cups closed but not fully tight, are degassed from sample adsorbed gas or dried sample from water or volatile material derived from prior pre-treatments (preparation).

According to the degassing mode, samples included in capsules, sometime also including carbon for reduction, are loaded into the sample housing 2, particularly into the carousel 1. After loading filled samples in cups in the carousel, the plate 3, acting as a lid, and the purge plug 14 are closed granting full tightness. Furthermore, the tank isolation valve 12 and the sampler isolation valve 17 are kept in the close configuration. In these conditions, the pump isolation valve 7 is opened, the pump P is activated and the heaters 19 are turned on. In this manner, the atmospheric gases, water vapor and other volatile material are removed from the samples by heating, and are pumped away from the sample housing 2.

A second possible operating mode is a "purging mode", which takes place after atmospheric gases are purged from the sample housing 2, and the samples to be analyzed also purged from gas adsorbed, water and volatile vapor, according to the degassing mode.

According to the purging mode, the pump isolation valve 7 and the sampler isolation valve 17 are kept closed, and the purge plug 14 is opened. The pressure regulators 10 and 16 are set to the each other closer pressure. At this stage, the gas cylinder isolation valve 12 is opened, so that the inert gas passes through the sample housing 2 and vents out the atmospheric gases through the gas vent 13. When purging is complete, the purge plug 14 is closed, the sampler isolation valve 17 is opened and the gas cylinder isolation valve 12 may be closed.

When a sampler 200 according to the third embodiment is used and a liquid injection is required, a preferring operating mode provides that after the samples are heated to the desired temperature, the liquid is injected by a syringe through the injection unit 22.

Afterwards, the system is allowed to equilibrate for the required time. Subsequently, pump P is activated in order to remove the exceeding vapour. Subsequently pump P is deactivated and pump isolation valve 7 is closed. Finally gas cylinder isolation valve 12 is opened and sampler isolation valve 17 is opened in order to start analysis.

From the above description, those skilled in the art will be able to appreciate how the sampler, according to the invention, allows the samples to be maintained in an inert gas environment within a fully sealed enclosure, thus preventing contamination from any atmospheric gases.

Furthermore, those skilled in the art will be able to see how the sampler according to the invention allows the samples to be degassed from any residual gas adsorbed or unwanted vapour in the samples eliminated before they are actually introduced into the elemental analyzer for analysis.

Furthermore, those skilled in the art will be able to see how the sampler according to the invention allows a simultaneous equilibration in a reduced time and an analytical sequential sampling of equilibrated samples.

Moreover, those skilled in the art will be able to appreciate how the sampler of the invention allows to obtain a procedure which achieve the so called "Identical Treatment" (IT) for all the samples thus obtaining a repeatability of the analysis.

Those skilled in the art, to the aim of meeting specific, contingent needs, will be able to make a number of adaptations, modifications, or replacements, of elements with others functionally equivalent to the described embodiments of the sampler according to the invention, without for this departing from the scope of the annexed claims.

What is claimed is:

1. Sampler, of the sealed fully tight type, for an elemental analyzer, comprising:

a sample housing suitable to accommodate one or more samples to be analyzed;

closure means suitable to reversibly seal said sample housing;

a sample passage having a connection opening for the passage of said sample from the sampler into the analyzer through said connection opening, comprising means for heating said sample housing and means for pumping out environmental gases and vapors from said sample housing;

a flushing duct connected or connectable to said sample passage and connected or connectable to a gas cylinder suitable to accommodate pressurized inert gas, said flushing duct being in fluid connection with said sample housing, such that the pressurized inert gas from the gas cylinder is capable of passing through said sample housing;

a carrier gas duct connected or connectable to said sample passage and connected or connectable to said gas cylinder, such that the pressurized inert gas from the gas cylinder is capable of passing through said connection opening of the sample passage to flow into the analyzer;

wherein said sample passage comprises sampler isolation valve means located in the sample passage between a first and a second gas port at which said flushing duct and said carrier gas duct are respectively connected with said sample passage, said sampler isolation valve means being configurable in at least an open configuration and a closed position.

2. Sampler according to claim 1, wherein said pumping means are suitable to generate a vacuum inside said sample housing.

3. Sampler according to claim 1, comprising pump isolation valve means operatively interposed between said pumping means and said sample housing, said pump isolation valve means being configurable in at least an open configuration, in which said pumping means are in fluid communication with said sample housing, and a close position, in which said sample housing is fluidly isolated from said pumping means.

4. Sampler according to claim 1, comprising a pumping duct for fluid connection between said sample housing and said pumping means, said pumping duct being located in the lower part of said sample housing.

5. Sampler according to claim 1, wherein said heating means comprise a plurality of heaters inserted into a sample housing body delimiting said sample housing.

6. Sampler according to claim 1, wherein said heating means comprise a temperature sensor inserted into a sample housing body delimiting said sample housing.

7. Sampler according to claim 5, wherein said temperature sensor is connected to a control unit suitable to control said heating means in dependence of the temperature read by said temperature sensor such as to maintain the temperature of said sampler housing at a substantially constant value.

8. Sampler according to claim 1, wherein said closure means comprise a closure plate being provided with a closable gas vent, such that gases passing through the sample housing can be purged out when the gas vent is opened.

9. Sampler according to claim 8, comprising a purge plug suitable to seal said gas vent of the closure plate.

10. Sampler according to claim 1, wherein said flushing duct comprises gas cylinder isolation valve means operatively disposed between said gas cylinder and said sample passage, said gas cylinder isolation valve means being configurable in at least an open configuration, in which said gas cylinder is in communication with said sample passage, and a close position, in which said gas cylinder is isolated from said sample passage.

11. Sampler according to claim 1, wherein said flushing duct comprises gas restriction means and a pressure regulator to control pressure of said inert gas when flowing through said flushing duct.

12. Sampler according to claim 1, wherein said carrier gas duct is disposed in parallel with said flushing duct.

13. Sampler according to claim 1, wherein said carrier gas duct comprises a pressure regulator.

14. Sampler according to claim 1, further comprising an injection unit suitable for injecting liquid in the sample housing.

15. Elemental analyzer comprising a sampler according to claim 1.

16. Sampler, of the sealed fully tight type, for an elemental analyzer, comprising:

a sample housing suitable to accommodate one or more samples to be analyzed;

closure means suitable to reversibly seal said sample housing;

a sample passage having a connection opening for the passage of said sample from the sampler into the analyzer through said connection opening, comprising means for heating said sample housing and means for pumping out environmental gases and vapors from said sample housing;

a flushing duct connected or connectable to said sample passage and connected or connectable to a gas cylinder suitable to accommodate pressurized inert gas, said flushing duct being in fluid connection with said sample housing, such that the pressurized inert gas from the gas cylinder is capable of passing through said sample housing;

a carrier gas duct connected or connectable to said sample passage and connected or connectable to said gas cylinder, such that the pressurized inert gas from the gas cylinder is capable of passing through said connection opening of the sample passage to flow into the analyzer;

an injection unit suitable for injecting liquid in the sample housing;

wherein said sample passage comprises sampler isolation valve means located in the sample passage between a first and a second gas port at which said flushing duct and said carrier gas duct are respectively connected with said sample passage, said sampler isolation valve means being configurable in at least an open configuration and a closed position.

17. Sampler according to claim 16, wherein said injection unit is configured to apply the liquid to all samples located within the sample housing simultaneously.

18. Sampler according to claim 17, wherein said injection unit comprises an injection port.

19. Sampler according to claim 18, wherein said liquid comprises water at a known isotope ratio.

20. Sampler according to claim 19, wherein said injection port is configured to receive a syringe.

* * * * *